United States Patent
Meyer

(10) Patent No.: US 10,036,792 B2
(45) Date of Patent: Jul. 31, 2018

(54) MAGNETIC RESONANCE SYSTEM WITH POSITION-DEPENDENT SLEW RATE LIMITATION

(71) Applicant: Heiko Meyer, Uttenreuth (DE)

(72) Inventor: Heiko Meyer, Uttenreuth (DE)

(73) Assignee: Siemens Aktiengesellschaft, München (DE)

(*) Notice: Subject to any disclaimer, the term of this patent is extended or adjusted under 35 U.S.C. 154(b) by 671 days.

(21) Appl. No.: 14/592,798

(22) Filed: Jan. 8, 2015

(65) Prior Publication Data

US 2015/0192652 A1 Jul. 9, 2015

(30) Foreign Application Priority Data

Jan. 8, 2014 (DE) .......................... 10 2014 200 147

(51) Int. Cl.
G01V 3/00 (2006.01)
G01R 33/54 (2006.01)
A61B 5/055 (2006.01)
G01R 33/28 (2006.01)

(52) U.S. Cl.
CPC ............ G01R 33/543 (2013.01); *A61B 5/055* (2013.01); *G01R 33/288* (2013.01)

(58) Field of Classification Search
CPC .............. G01R 33/543; G01R 33/5659; G01R 33/3415; G01R 33/36; A61B 5/055
USPC ........................................................ 324/309
See application file for complete search history.

(56) References Cited

U.S. PATENT DOCUMENTS

| 5,198,769 A | 3/1993 | Frese et al. |
| 6,198,282 B1* | 3/2001 | Dumoulin .......... G01R 33/3852 324/307 |
| 2003/0098687 A1 | 5/2003 | Arneth et al. |
| 2003/0098688 A1 | 5/2003 | Brinker et al. |
| 2004/0075434 A1* | 4/2004 | Vavrek ................. G01R 33/385 324/318 |
| 2004/0189298 A1 | 9/2004 | Vavrek et al. |
| 2006/0197528 A1 | 9/2006 | Bielmeier et al. |
| 2007/0096735 A1 | 5/2007 | Morich et al. |

(Continued)

FOREIGN PATENT DOCUMENTS

| DE | 10150137 A1 | 5/2003 |
| DE | 10150138 A1 | 5/2003 |

(Continued)

OTHER PUBLICATIONS

German office Action for related German Application No. 10 2014 200 147.1 dated Apr. 14, 2016, with English Translation.

(Continued)

*Primary Examiner* — Walter L Lindsay, Jr.
*Assistant Examiner* — Frederick Wenderoth
(74) *Attorney, Agent, or Firm* — Lempia Summerfield Katz LLC

(57) ABSTRACT

A control facility of a magnetic resonance system receives parameters of a measuring sequence from an operator. The parameters define an activation of a gradient system of the magnetic resonance system. The control facility detects an exposure of at least one body region of the examination object brought about by the activation of the gradient system. The exposure is detected as a function of the position in which the examination object is disposed in an examination volume of the magnetic resonance system.

16 Claims, 5 Drawing Sheets

(56) References Cited

U.S. PATENT DOCUMENTS

| | | | |
|---|---|---|---|
| 2009/0146660 A1* | 6/2009 | Schnell | G01R 33/3607 324/318 |
| 2010/0308829 A1 | 12/2010 | Vu et al. | |
| 2011/0152665 A1 | 6/2011 | Lai | |
| 2015/0002147 A1* | 1/2015 | Fontius | G01R 33/288 324/309 |

FOREIGN PATENT DOCUMENTS

| | | |
|---|---|---|
| DE | 102005007895 A1 | 8/2006 |
| DE | 102007059522 A1 | 6/2009 |

OTHER PUBLICATIONS

H. Homann et al.: "Validation and Comparison of Patient-Specific SAR Models" in Proc. Intl. Soc. Mag. Reson. Med.; vol. 19; pp. 489; 2011.

Zhang B., et.al: "Peripheral-Nerve-Stimulation-Optimized Gradient Waveform Design", in: Proc. Intl. Soc. Mag. Reson. Med. vol. 10.; 2002.

German Office Action for German Application No. 0 2014 200 147.1, dated Dec. 10, 2014 with English Translation.

\* cited by examiner

FIG 5

| p1 | p2 | ... |
|----|----|----|
| L1 | L2 | |
| X1 | X2 | |
| Y1 | Y2 | |
| ⋮ | ⋮ | |

MAGNETIC RESONANCE SYSTEM WITH POSITION-DEPENDENT SLEW RATE LIMITATION

This application claims the benefit of DE 10 2014 200 147.1, filed on Jan. 8, 2014, which is hereby incorporated by reference in its entirety.

BACKGROUND

The present embodiments relate to a magnetic resonance system with position-dependent slew rate limitation.

Exemplary modification of pulse sequences is provided, for example, by US 2010/0308829 A1.

In magnetic resonance systems, the gradient system switches gradient fields in order to encode the detected magnetic resonance signals in the spatial domain and/or in the frequency domain. In this process, the speed with which field changes are generated (e.g., slew rate) is directly linked to the image quality achieved and the measuring time required to perform the measurement. The faster the field changes are performed, the shorter the resulting measuring times. Distortion and artifacts may also be reduced. The prior art therefore attempts to perform field changes as quickly as possible.

However, the gradient fields that vary over time induce currents in the human body. These currents may cause peripheral nerves to be stimulated. Experts refer to this as peripheral nerve stimulation (PNS). In extreme instances, the gradient fields that vary over time may even cause stimulation of the heart muscle. Such stimulation may result in serious damage to health and in some circumstances even death for the patient. There are therefore statutory limit values that magnetic resonance systems may not exceed during operation. Compliance with such limit values is provided by a monitoring function that is implemented in the control facility of the magnetic resonance system. This monitoring function is often referred to as the gradient system watchdog (GSWD). The monitoring function implements an operating method.

The induction of currents and the corresponding stimulation of peripheral nerves are a function of different factors. One influencing factor is the design of the gradient coil system. A further influencing factor is the pulse sequence. The position of the patient or the examination object within the examination volume also plays a significant role. For example, the stimulation of peripheral nerves for a defined gradient pulse is greater when the ribcage of the patient is located in the isocenter of the magnetic resonance system than when the feet of the patient are located in the isocenter.

In the prior art (e.g., the abovementioned US 2010/0 308 829 A1), the worst possible scenario is always assumed. A worst case approach is therefore taken.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an imaging with reduced measuring sequence duration and fewer artifacts is provided without endangering an examination object.

According to one or more of the present embodiments, an operating method is configured such that exposure is detected as a function of the position in which the examination object is disposed in an examination volume of the magnetic resonance system.

The term "position" may refer only to a translational position. The term "orientation" is used for a rotational orientation.

In one embodiment, the operator of the magnetic resonance system positions the examination object roughly first. Such positioning may be performed based on medical/anatomical factors without precise consideration of the implementation of threshold value monitoring. If the examination object is disposed unfavorably in the context of such positioning (e.g., if the ribcage of the examination object is located in the isocenter of the magnetic resonance system), it is not possible to achieve accelerated execution using the procedure of one or more of the present embodiments. However, accelerated execution may be provided in many instances.

In one embodiment, the control facility may receive the position of the examination object in the examination volume from the operator or, provisionally, may determine the position. Different embodiments of the operating method may be provided.

For example, the control facility may compare the detected exposure with an exposure limit value and, depending on whether the detected exposure is below or above the exposure limit value, may activate the magnetic resonance system according to the predetermined measuring sequence or to institute other measures.

The other measures may include, for example, if the detected exposure is above the exposure limit value, the control facility modifying the measuring sequence so that an exposure resulting for the modified measuring sequence is below the exposure limit value and activating the magnetic resonance system according to the modified measuring sequence, and/or not allowing the execution of the measuring sequence and outputting a corresponding notification to the operator.

The same measures may be instituted as in the prior art. For example, the modification may include temporal scaling with or without corresponding scaling of the amplitude of the gradient pulses and, if necessary, also of the high-frequency pulses (e.g., temporally and/or with respect to amplitude), as in the prior art. According to one or more of the present embodiments, however, if the detected exposure is above the exposure limit value, the control facility may detect an exposure of the at least one body region of the examination object brought about by the activation of the gradient system using the measuring sequence for at least one further position of the examination object as a function of this further position. It is therefore possible for the control facility to detect one or at least one alternative position, in which the exposure limit value is not exceeded despite an unchanged measuring sequence or a measuring sequence that is simply adjusted based on the changed position.

If the control facility may detect at least one such further position (e.g., if the detected exposure of the at least one body region is below the exposure limit value for at least one of the further positions of the examination object), the control facility may, for example, select one of these positions, position the examination object in the selected position, and activate the magnetic resonance system according to the measuring sequence. Alternatively, the control facility may, for example, offer the positions in which the exposure limit value is not exceeded to the operator for selection.

If, however, the control facility cannot detect any such further position (e.g., if the detected exposure of the at least one body region is not below the exposure limit value for any of the further positions), the control facility may, for example, modify the measuring sequence so that an exposure resulting for the modified measuring sequence is below the exposure limit value for at least one of the positions (e.g., the received position or one of the further positions), position the examination object in this position, and activate the magnetic resonance system according to the modified measuring sequence. Alternatively or additionally, the control facility may not allow the execution of the measuring sequence and may output a corresponding notification to the operator. In one embodiment, the received position and/or the further positions and/or selected further positions may be offered the operator for selection. If the measuring sequence is modified by the control facility (e.g., compulsorily because the exposure limit value has been exceeded), the control facility may determine the position such that the necessary modification of the measuring sequence is kept as minor as possible. Alternatively or additionally, other criteria such as, for example, expected artifacts and the like may be considered.

In one embodiment, the control facility may use the position received from the operator to detect an exposure of the at least one body region of the examination object brought about by the activation of the gradient system for at least one further position of the examination object as a function of this further position. The control facility may compare the detected exposure with the exposure limit value. This procedure is therefore also possible, for example, if the exposure detected for the received position already does not exceed the exposure limit value. A better position of the examination object may therefore be proposed to the operator of the magnetic resonance system if the position predetermined by the operator is permissible but unfavorable.

Alternatively, the operator may not predetermine a position for the control facility. The control facility then automatically determines the position of the examination object and at least one further position of the examination object. The control facility then also detects a respective exposure of the at least one body region of the examination object brought about by the activation of the gradient system for the further positions of the examination object as a function of the respective further position. The control facility may then automatically detect an optimum position regardless of any position predetermined by the operator or may propose a number of permissible positions to the operator, so that the operator may make a permissible selection. In one embodiment, the positions and associated exposure values may be outputted to the operator so that the operator may select a suitable position.

If the control facility compares the detected exposures with an exposure limit value, and the detected exposure of the at least one body region is below the exposure limit value for at least one of the positions of the examination object, the control facility may select one of these positions. The control facility may position the examination object in the selected position and may activate the magnetic resonance system according to the measuring sequence or offer the positions (e.g., the positions for which the exposure limit value is not exceeded) to the operator for selection.

If, however, the detected exposure is above the exposure limit value for all the positions determined, the control facility may modify the measuring sequence so that an exposure detected for the modified measuring sequence is below the exposure limit value for at least one of the positions. The control facility may position the examination object in this position and may activate the magnetic resonance system according to the modified measuring sequence. As before, the modification may include, for example, a temporal scaling with or without corresponding scaling of the amplitude of the gradient pulses. If necessary, high-frequency pulses may also be scaled temporally and/or with respect to amplitude. Alternatively or additionally, the control facility may not allow the execution of the measuring sequence and may output a corresponding notification to the operator.

In any instance, the control facility may output the detected exposure to the operator with assignment to the position of the examination object. This gives the operator feedback about the resulting exposure. The operator may use this information, for example, to vary the measuring sequence and/or the position of the examination object. If the operator determines, for example, that the resulting exposure is significantly below the exposure limit value, in some circumstances, the operator may vary parameters of the measuring sequence so that higher but still permissible (e.g., below the exposure limit value) exposure results.

In one embodiment, the control facility may output further assessment criteria for the position of the examination object to the operator. One example of such an assessment criterion is the extent to which the examination object will be offset compared with an ideal position that may be preferred for reasons relating to the examination if the selected position is selected. Further possible criteria may be, for example, the size of the expected artifacts (e.g., including aliasing, flux, fat suppression, homogeneity volume, distortions) or other constraints such as the position and/or number of local receive coils.

In one embodiment, the control facility may take both the position and orientation of the examination object into account when detecting the exposure of the at least one body region of the examination object.

A computer program is also provided. The computer program may be stored on a non-transitory computer-readable storage medium. The computer program includes machine codes having instructions executable by the control facility (e.g., one or more processors). According to one or more of the present embodiments, the processing of the machine code by the control facility causes the control facility to execute an operating method.

A control facility is also provided. According to one or more of the present embodiments, the control facility is programmed using a computer program of one or more of the present embodiments.

A magnetic resonance system is provided. According to one or more of the present embodiments, the control facility is configured such that the control facility executes an operating method of one or more of the present embodiments during operation.

BRIEF DESCRIPTION OF THE DRAWINGS

FIG. 5 shows an exemplary output mask.

DETAILED DESCRIPTION

Figure 1:
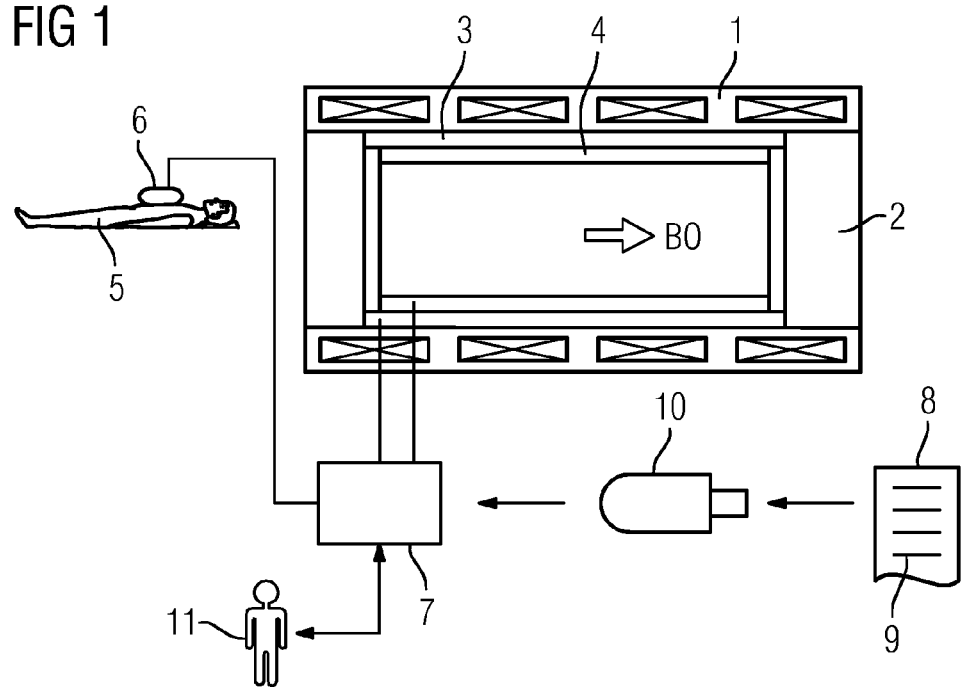
FIG. 1 shows one embodiment of a magnetic resonance system.

According to FIG. 1, one embodiment of a magnetic resonance system includes a base magnet 1. The base magnet 1 generates a temporally static, spatially essentially homogeneous base magnetic field B0 in an examination volume 2. The base magnet 1 may be configured, for example, as a superconducting magnet.

The magnetic resonance system also includes a gradient system 3. The gradient system 3 generates gradient fields that are superimposed on the base magnetic field B0. The gradient system 3 or gradient fields bring(s) about encoding of magnetic resonance signals in the spatial domain and/or in the frequency domain.

The magnetic resonance system also includes at least one high-frequency coil 4. The high-frequency coil 4 may be used to stimulate an examination object 5 (e.g., a person) disposed in the examination volume 2 to emit magnetic resonance signals. The magnetic resonance signals stimulated may be received using the high-frequency coil 4 or a further high-frequency coil 6.

The magnetic resonance system also includes a control facility 7 (e.g., a controller, a processor). The control facility 7 is operable to activate at least the gradient system 3 and the high-frequency coils 4, 6. The control facility 7 is configured as a software-programmable control facility. The control facility 7 is programmed using a computer program 8.

The computer program 8 includes machine code 9 that may be processed by the control facility 7. The processing of the machine code 9 by the control facility 7 causes the control facility 7 to execute an operating method of one or more of the present embodiments. The programming of the control facility 7 using the computer program 8 therefore causes the control facility 7 to be configured accordingly. The operating method is described in more detail below in conjunction with FIGS. 2 to 7.

The computer program 8 may be supplied to the control facility 7 in any manner. FIG. 1 shows a data medium 10, purely by way of example, on which the computer program 8 may be stored in machine-readable form (e.g., in electronic form). The illustration of the data medium 10 as a USB memory stick is, however, purely exemplary. The data medium 10 may also be configured differently.

Figure 2:
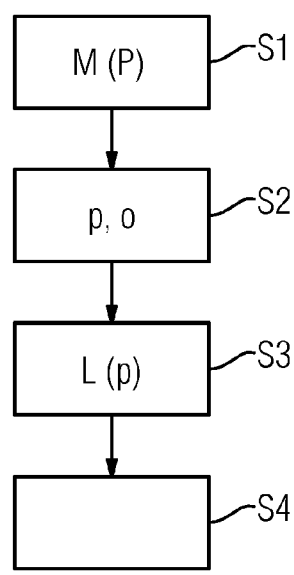
FIGS. 2 to 4 show exemplary flow diagrams.

According to FIG. 2, in act S1, the control facility 7 receives parameters P of a measuring sequence M from an operator 11. The parameters P as a whole define an activation of the gradient system 3 and the high-frequency coils 4, 6. In the context of one or more of the present embodiments, the parameters P define the activation of the gradient system 3.

In act S2, at least one position p of the examination object 5 is also made known to the control facility 7. The position p is purely translational. In some instances an orientation o (e.g., rotational orientation) of the examination object 5 may be made known to the control facility 7 in act S2 in addition to the position p. As part of act S2, the control facility 7 may determine the position p automatically. Alternatively, the position p may be predetermined for the control facility 7 by the operator 11 (see FIG. 1). These two options are examined in more detail below in conjunction with the further FIGS. Only the position p is examined in more detail below in the context of the further implementation of the operating methods. The orientation o is not mentioned further. The orientation o may, however, be taken into account in addition to the position p.

In act S3, the control facility detects an exposure L. The exposure L corresponds to the exposure of a body region of the examination object 5 (e.g., the ribcage of the examination object 5) brought about by the activation of the gradient system 3 according to the measuring sequence M when the examination object 5 is positioned according to the position p of act S2. The detection in act S3 therefore takes place as a function of the position p in which the examination object 5 is disposed in the examination volume 2. After act S3 in act S4, further measures are instituted based on the detection in act S3.

One embodiment of the procedure in FIG. 2 is described below in conjunction with FIG. 3, with the control facility 7 receiving the position p of the examination object 5 in the examination volume 2 from the operator 11.

Figure 3:
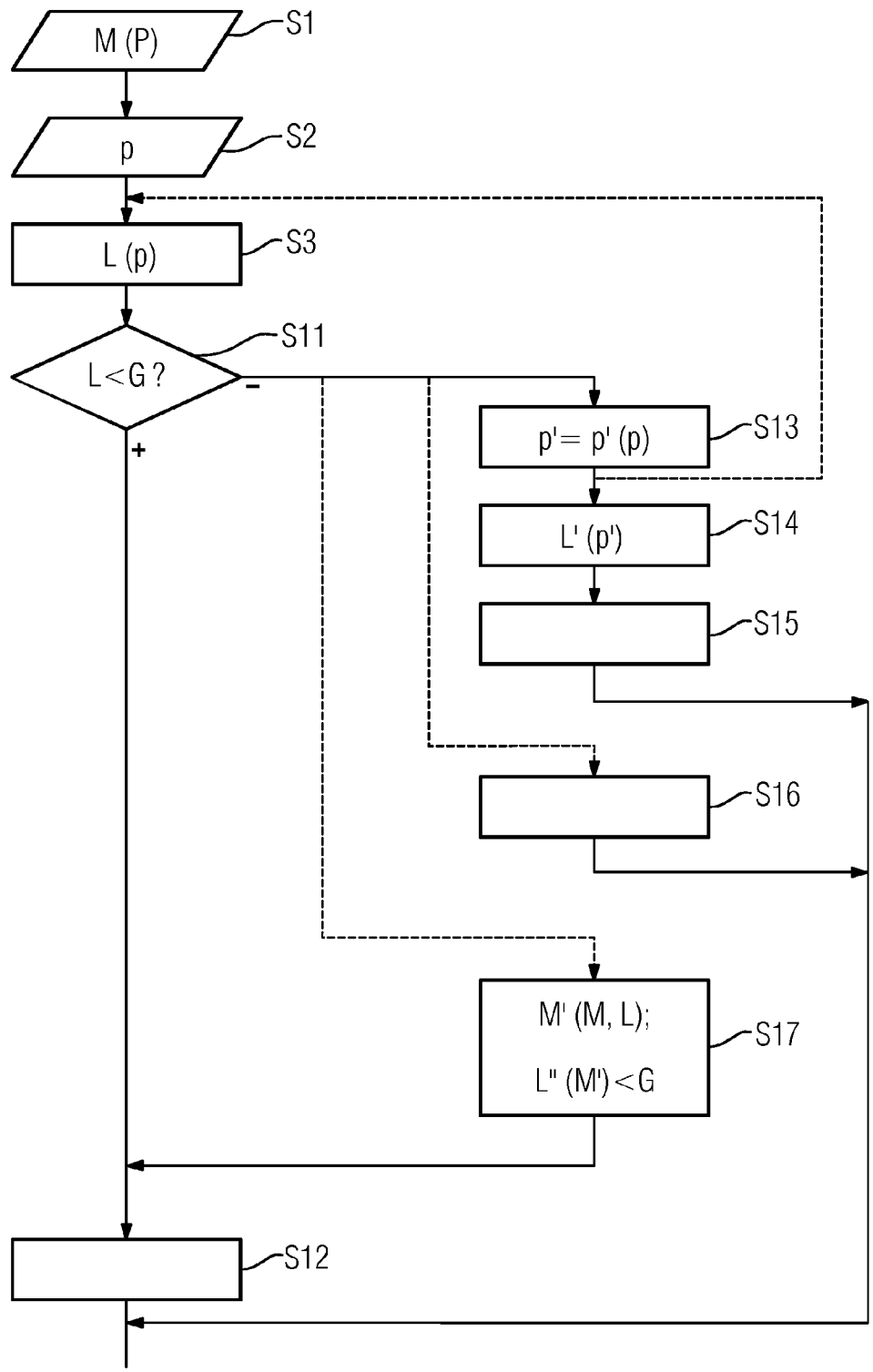

Acts S1 to S3 are also present as part of the procedure in FIG. 3. The embodiment in FIG. 3 therefore relates to act S4 in FIG. 2.

According to FIG. 3 in act S11, the control facility 7 compares the exposure L detected in act S3 with an exposure limit value G. If the detected exposure L is below the exposure limit value G, the control facility 7 proceeds to act S12. In act S12, the control facility 7 activates the magnetic resonance system (e.g., the gradient system 3 and the high-frequency coils 4, 6) according to the predetermined measuring sequence M. If necessary, positioning of the examination object 5 according to the position p predetermined in act S2 also takes place as part of act S12. However, if the detected exposure L is above the exposure limit value G, the control facility 7 institutes other measures. Examples of such measures are also shown in FIG. 3. Such measures may be implemented individually according to the diagram in FIG. 3. However, such measures may also be implemented in combinations or all together. Other measures may also be provided.

According to the diagram in FIG. 3, the control facility 7 may, for example, determine at least one further position p' in act S13 (e.g., starting from the position p predetermined in act S2). If necessary, the measuring sequence M may be modified for this purpose as part of act S13, so that despite the different positioning of the examination object 5, the detected magnetic resonance signals originate from the same region of the examination object 5 as before the determination of the at least one further position p'. This modification may include, for example, an adjustment of the high-frequency transmit pulses and/or the sampling of the received magnetic resonance signals. Other modifications of the measuring sequence M are, however, not undertaken as part of act S13. The region of the examination object 5 may alternatively be the abovementioned body region or another body region of the examination object 5. In act S14, as in act S3, the control facility 7 then detects an exposure L' of the at least one body region of the examination object 5 brought about by the activation of the gradient system 3 using the measuring sequence M (optionally modified in act S13) as a function of this further position p'.

If just one further position p' is determined in act S13, in some circumstances, act S14 may be omitted. It is then, for example, possible to proceed directly from act S13 to act 3 according to the broken line in FIG. 3. If the control facility 7 proceeds by way of this alternative route to act S12, however, the examination object 5 is to be positioned in the further position p' before act S12 is executed. Alternatively, act S14 may be present, and in act S15, a further (e.g., any) measure may be instituted after act 14 has been executed. For example, the at least one further position p' and the associated exposure L' detected in act S14 may be output to the operator 11.

Alternatively or additionally, the control facility 7 may proceed to act S16. In act S16, the control facility 7 does not allow the execution of the measuring sequence M. Alternatively or additionally, the control facility 7 may output a corresponding notification to the operator 11 as part of act S16. For example, a message with the content "exposure too high" may be output to the operator 11, optionally in conjunction with information about the extent to which the exposure limit G has been exceeded.

Alternatively or additionally, again, the control facility 7 may proceed to act S17. In act S17, the control facility 7 modifies the measuring sequence M. The modification takes place such that for the modified measuring sequence, referred to below with the reference character M' to distinguish from the original measuring sequence M, a resulting exposure L" is below the exposure limit value G. For example, temporal scaling may take place with or without adjustment of the amplitude of the gradient pulses. If necessary, high-frequency pulses may also be scaled temporally and/or with respect to amplitude as part of act S17. The control facility then proceeds to act S12. As a result, the magnetic resonance system (e.g., the gradient system 3) is therefore activated according to the modified measuring sequence M' in the context of this procedure.

As part of the further measures in act S15, different measures may be instituted. This is described in more detail below in conjunction with FIG. 4. In the context of the procedure according to FIG. 4, it is assumed that a number of further positions p' are determined as part of act S13. However, this is not necessarily the case. A single further position p' may be determined.

Figure 4:
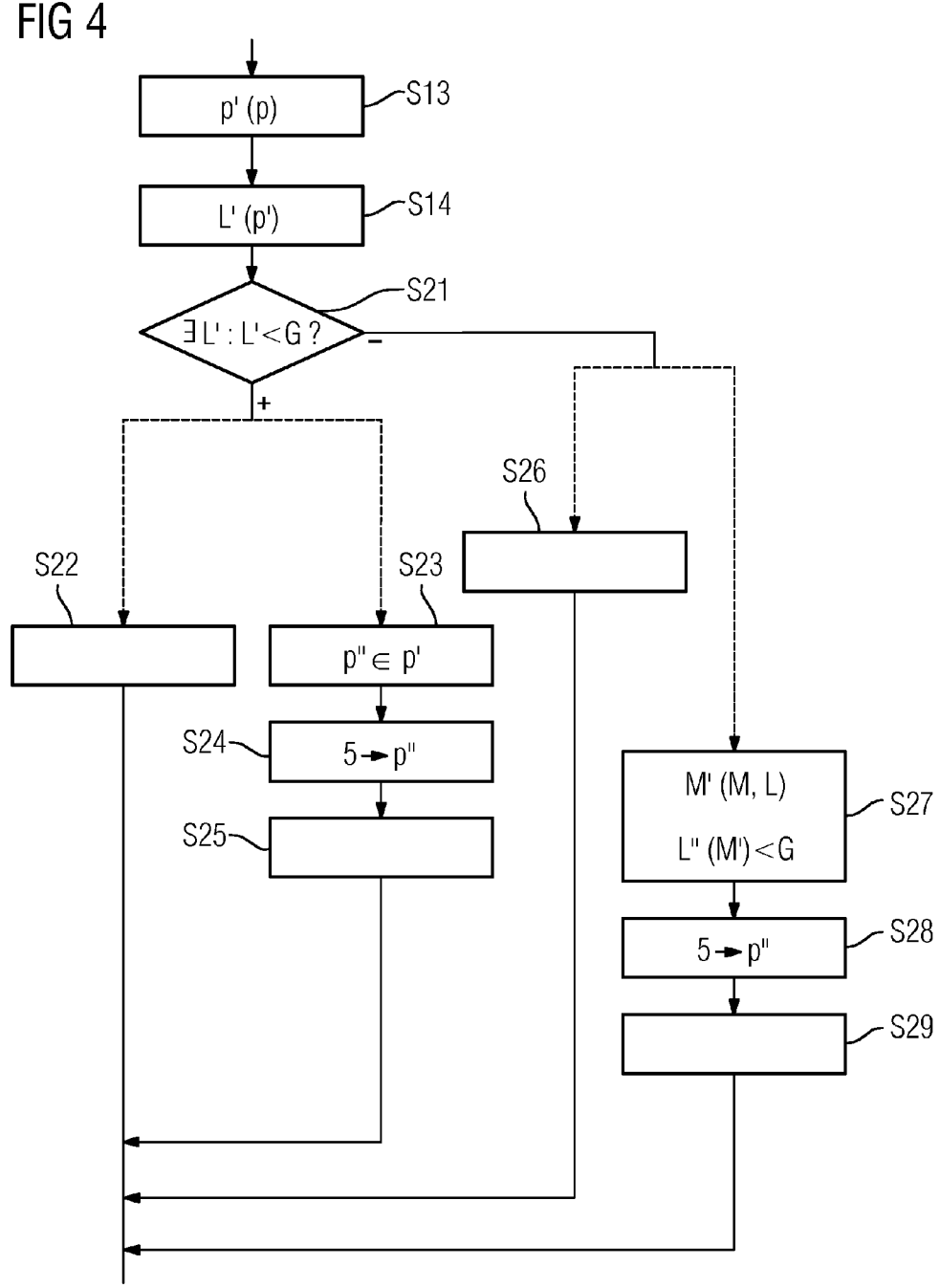

In the context of the procedure in FIG. 4, acts S13 and S14 are initially present, as in FIG. 3. In act S21, the control facility 7 checks whether the detected exposure L' of the at least one body region of the examination object 5 is below the exposure limit value G for at least one of the further positions p'. The check takes place under the assumption that the magnetic resonance system is activated according to the measuring sequence M that is unchanged or has only been modified according to act S13.

Figure 5:
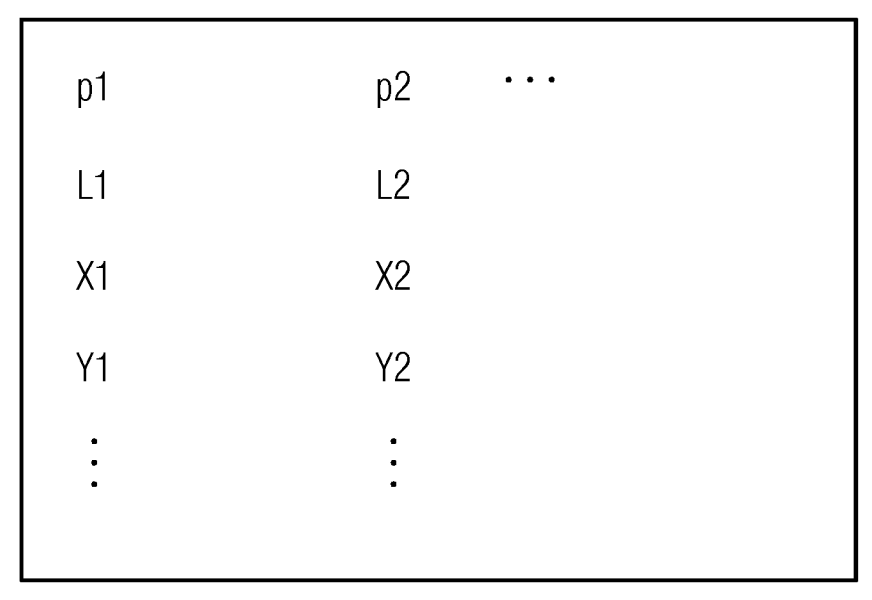

If the result of the check in act S21 is positive, the control facility 7 has been able to find at least one such position p'. In this instance, the control facility 7 may proceed to act S22. In act S22, the control facility 7 undertakes an output to the operator 11. For example, in act S22, the control facility 7 offers these further positions p', in which therefore the detected exposure L' is below the exposure limit G, to the operator 11 for selection. For example, the corresponding further positions p' may be output together with the respective exposure value L'. Further information of relevance to the assessment of the respective further position p' may also optionally be output. FIG. 5 shows such an output purely by way of example. The further positions p' are shown in FIG. 5 as p1, p2, etc. Similarly, the associated exposure values L' are shown as L1, L2, etc., and the associated further relevant information is shown as X1, X2, etc. and Y1, Y2, etc. in FIG. 5.

Alternatively, the control facility 7 may proceed to act S23. In act S23, the control facility 7 selects one of these further positions p'. The selection criterion may be, for example, that the relevant body region of the examination object 5 is subject to as little exposure as possible. However, other assessment criteria may be provided, and the other assessment criteria may be taken into account as alternatives or additions. Examples of such assessment criteria are expected artifacts or other constraints such as the position and/or number of local receive coils. The selected further position p' is referred to as the selected position and shown with the reference character p" below to distinguish from other positions p, p'.

In act S24, the control facility 7 positions the examination object 5 in the selected position p". In act S25, the control facility 7 then activates the magnetic resonance system (e.g., the gradient system 3 and the high-frequency coils 4, 6) using the measuring sequence M, which is assigned to the selected position p".

If, however, the result of the check in act S21 is negative (e.g., the detected exposure L' of the at least one body region of the examination object 5 is not below the exposure limit value G for any of the further positions p' during activation of the magnetic resonance system using the measuring sequence M), the control facility 7 proceeds to act S26.

In act S26, as in act S16, the control facility 7 does not allow the execution of the measuring sequence M. Alternatively or additionally, the control facility 7 may output a corresponding notification to the operator 11 as part of act S26. For example, a message with the content "exposure too high for all alternative positions" may be output to the operator 11, optionally in conjunction with information about the extent to which the exposure limit G is exceeded.

Alternatively or additionally, again the control facility 7 may proceed to act S27. In act S27, as in act S17, the control facility 7 modifies the measuring sequence M. The modification takes place such that for the modified measuring sequence, referred to below with the reference character M' to distinguish from the original measuring sequence M, the exposure L" resulting for the modified measuring sequence M' is below the exposure limit value G for at least one of the positions p, p'. The relevant position p, p' may alternatively be the position p predetermined as part of act S2 or one of the further positions p'.

The control facility 7 then proceeds to act S28. In act S28, the control facility 7 positions the examination object 5 in the position for which the resulting exposure L" is now below the exposure limit G.

The control facility 7 then proceeds to act S29. As far as content is concerned, act S29 corresponds to act S12. In act S29, therefore, the magnetic resonance system (e.g., the gradient system 3) is activated according to the modified measuring sequence M'.

Figure 6:
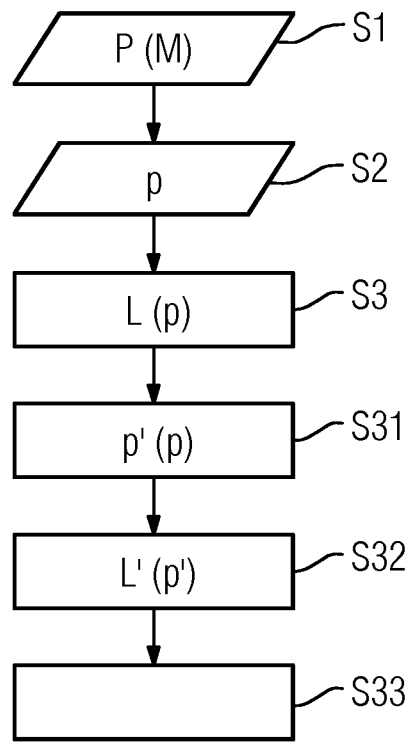
FIGS. 6 and 7 show exemplary flow diagrams.
Figure 7:
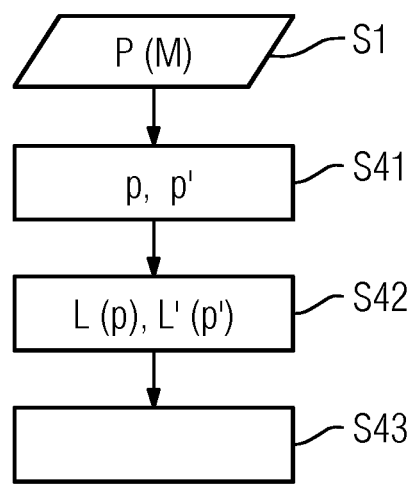

FIG. 6 shows a further embodiment of act S4 in FIG. 2 as an alternative to FIGS. 3 and 4. According to FIG. 6 in act S31, the control facility 7 detects at least one further position p' of the examination object 5 (e.g., a number of further positions p'). The control facility 7 detects the further positions p' based on the position p received in act S2. If necessary, the measuring sequence M may be modified for this purpose as part of act S31, so that despite the different positioning of the examination object 5, the detected magnetic resonance signals originate from the same region of the examination object 5 as before the determination of the at least one further position p'. The corresponding possible modifications have already been mentioned above. Other modifications of the measuring sequence M are, however, not undertaken as part of act S31.

In act S32, the control facility 7 detects an exposure L' of the at least one body region of the examination object 5 brought about by the activation of the gradient system 3 according to the measuring sequence M in each instance for the further positions p'.

In act S33, the control facility 7 institutes further measures based on the detection in act S3 and the detections in act S32. In the simplest instance, as described above in conjunction with act S22 in FIG. 4, the positions p', the exposures L' and further relevant information X, Y may be output. Alternatively, as set out above in conjunction with FIGS. 3 and 4 (e.g., act S23 to S25 in FIG. 4), an independent selection of one of the positions p, p', a modification of the measuring sequence M, not allowing the execution of the measuring sequence M, or any combination thereof may be provided.

As an alternative to the procedure described above in conjunction with FIGS. 2 to 6, the operator 11 may not predetermine a position p of the examination object 5 for the control facility 7. In this instance, the control facility 7 receives the measuring sequence M or corresponding parameters P according to FIG. 7, but in act S1. Act S2 is, however, replaced by act S41. In act S41, the control facility 7 automatically determines the position p and at least one further position p' of the examination object 5. The control facility 7 may also determine a number of further positions p' in addition to the position p. If necessary, the measuring sequence M may be modified in each instance as part of act S41 so that despite the respective positioning of the examination object 5, the detected magnetic resonance signals originate from the same region of the examination object 5. Other modifications of the measuring sequence M are, however, not undertaken as part of act S41.

In act S42, the control facility 7 detects an exposure L, L' of the at least one body region of the examination object 5 brought about by the activation of the gradient system 3 according to the respective measuring sequence M in each instance for the position p and the further positions p'.

In act S43, the control facility 7 institutes further measures based on the detections in act S42. In the simplest instance, as described above in conjunction with FIG. 4, the positions p, p', the exposures L, L' and further relevant information X, Y may be output. Alternatively, as set out above in conjunction with FIG. 4, an independent selection of one of the positions p, p', a modification of the measuring sequence M, not allowing the execution of the measuring sequence, or any combination thereof may be provided.

A control facility 7 of a magnetic resonance system receives parameters P of a measuring sequence M from an operator 11. The parameters P define an activation of a gradient system 3 of the magnetic resonance system. The control facility 7 detects an exposure L of at least one body region of the examination object 5 brought about by the activation of the gradient system 3. The exposure L is detected as a function of the position p in which the examination object 5 is disposed in an examination volume 2 of the magnetic resonance system.

The present embodiments have many advantages. For example, a measuring sequence M may be executed in a time-optimized manner (e.g., as quickly as possible) and still safely provide that the patient (e.g., the examination object 5) is not endangered. Further criteria such as, for example, expected image quality may be taken into account as part of the optimization.

Although the invention has been illustrated and described in greater detail using the exemplary embodiments, the invention is not restricted by the disclosed examples, and other variations may be derived therefrom by the person skilled in the art without departing from the scope of protection of the invention.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An operating method for a controller of a magnetic resonance system, the operating method comprising:
   receiving, by the controller, parameters of a predetermined measuring sequence from an operator, wherein the parameters define an activation of a gradient system of the magnetic resonance system;
   detecting, by the controller, an exposure of at least one body region of an examination object brought about by the activation of the gradient system, wherein detecting the exposure comprises detecting the exposure as a function of a position in which the examination object is disposed in an examination volume of the magnetic resonance system;
   storing, by a non-transitory computer-readable storage medium, the detected exposure;
   comparing, by the controller, the detected exposure with an exposure limit value; and
   depending on whether the detected exposure is below or above the exposure limit value, activating the magnetic resonance system according to the predetermined measuring sequence or instituting other measures.

2. The operating method of claim 1, further comprising:
   receiving, by the controller, the position of the examination object in the examination volume from the operator; or
   determining, by the controller, the position of the examination object in the examination volume.

3. The operating method of claim 1, wherein when the detected exposure is above the exposure limit value, the operating method further comprises modifying, by the controller, the measuring sequence so that an exposure resulting for the modified measuring sequence is below the exposure limit value and activating, by the controller, the magnetic resonance system according to the modified measuring sequence, preventing, by the controller, the execution of the measuring sequence and outputting, by the controller, a corresponding notification to the operator, detecting, by the controller, an exposure of the at least one body region of the examination object brought about by the activation of the gradient system using the measuring sequence for at least one further position of the examination object as a function of the at least one further position, or any combination thereof.

4. The operating method of claim 3, further comprising:
   when the exposure of the at least one body region is below the exposure limit value for at least one of the further positions of the examination object:
      selecting, by the controller, a position of the at least one further position, positioning, by the controller, the examination object in the selected position, and activating the magnetic resonance system according to the measuring sequence; or
      offering the at least one further position to the operator for selection; and when the detected exposure of the at least one body region is not below the exposure limit value for any further position of the at least one further position:
modifying, by the controller, the measuring sequence so that an exposure resulting for the modified measuring sequence is below the exposure limit value for one or more positions of the position and the at least one further position;
positioning, by the controller, the examination object in the one or more positions; and
activating, by the controller, the magnetic resonance system according to the modified measuring sequence, preventing the execution of the measuring sequence and outputting a corresponding notification to the operator, or a combination thereof.

5. The operating method of claim 2, further comprising:
detecting, by the controller, an exposure of the at least one body region of the examination object brought about by the activation of the gradient system for at least one further position of the examination object as a function of the at least one further position, the detecting of the exposure for the at least one further position comprising using the position received from the operator; and
comparing the detected exposure for the at least one further position with the exposure limit value.

6. The operating method of claim 1, further comprising:
automatically determining, by the controller, the position of the examination object and at least one further position of the examination object; and
detecting, by the controller, a respective exposure of the at least one body region of the examination object brought about by the activation of the gradient system for the at least one further position of the examination object as a function of the respective further position.

7. The operating method of claim 6, further comprising:
comparing, by the controller, the detected exposures with an exposure limit value;
when the detected exposure of the at least one body region is below the exposure limit value for at least one of the positions of the examination object:
selecting, by the controller, one of the positions, positioning, by the controller, the examination object in the one selected position, and activating, by the controller, the magnetic resonance system according to the measuring sequence; or
offering, by the controller, the positions to the operator for selection; and
when the detected exposure is above the exposure limit value for all the positions determined:
modifying, by the controller, the measuring sequence so that an exposure detected for the modified measuring sequence is below the exposure limit value for at least one of the positions, positioning, by the controller, the examination object in the at least one position, and activating the magnetic resonance system according to the modified measuring sequence, preventing the execution of the measuring sequence and outputting a corresponding notification to the operator, or a combination thereof.

8. The operating method of claim 1, further comprising outputting, by the controller, the detected exposure to the operator with assignment to the position of the examination object.

9. The operating method of claim 8, further comprising outputting, by the controller, further assessment criteria for the position of the examination object to the operator.

10. The operating method of claim 1, wherein detecting the exposure of the at least one body region of the examination object comprises the controller taking both the position and orientation of the examination object into account.

11. In a non-transitory computer-readable storage medium storing a computer program having machine code with instructions executable by a controller for a magnetic resonance system to operate the magnetic resonance system, the instructions comprising:
receiving, by the controller, parameters of a predetermined measuring sequence from an operator, wherein the parameters define an activation of a gradient system of the magnetic resonance system;
detecting, by the controller, an exposure of at least one body region of an examination object brought about by the activation of the gradient system, wherein detecting the exposure comprises detecting the exposure as a function of a position in which the examination object is disposed in an examination volume of the magnetic resonance system;
storing, by the non-transitory computer-readable storage medium, the detected exposure;
comparing the detected exposure with an exposure limit value; and
depending on whether the detected exposure is below or above the exposure limit value, activating the magnetic resonance system according to the predetermined measuring sequence or instituting other measures.

12. The non-transitory computer-readable storage medium of claim 11, wherein the instructions further comprise:
receiving the position of the examination object in the examination volume from the operator; or
determining the position of the examination object in the examination volume.

13. The non-transitory computer-readable storage medium of claim 11, wherein when the detected exposure is above the exposure limit value, the instructions further comprise modifying the measuring sequence so that an exposure resulting for the modified measuring sequence is below the exposure limit value and activating the magnetic resonance system according to the modified measuring sequence, preventing the execution of the measuring sequence and outputting a corresponding notification to the operator, detecting an exposure of the at least one body region of the examination object brought about by the activation of the gradient system using the measuring sequence for at least one further position of the examination object as a function of the at least one further position, or any combination thereof.

14. The non-transitory computer-readable storage medium of claim 13, wherein the instructions further comprise:
when the exposure of the at least one body region is below the exposure limit value for at least one of the further positions of the examination object:
selecting a position of the at least one further position, positioning the examination object in the selected position, and activating the magnetic resonance system according to the measuring sequence; or
offering the at least one further position to the operator for selection; and
when the detected exposure of the at least one body region is not below the exposure limit value for any further position of the at least one further position:
modifying the measuring sequence so that an exposure resulting for the modified measuring sequence is below the exposure limit value for one or more positions of the position and the at least one further position;

positioning the examination object in the one or more positions; and activating the magnetic resonance system according to the modified measuring sequence, preventing the execution of the measuring sequence and outputting a corresponding notification to the operator, or a combination thereof.

15. A control facility for a magnetic resonance system, the control facility comprising:

a processor configured to:

receive parameters of a predetermined measuring sequence from an operator, wherein the parameters define an activation of a gradient system of the magnetic resonance system;

detect an exposure of at least one body region of an examination object brought about by the activation of the gradient system, wherein the detection of the exposure comprises detection of the exposure as a function of a position in which the examination object is disposed in an examination volume of the magnetic resonance system;

store, on a non-transitory computer-readable storage medium, the detected exposure;

compare, by the controller, the detected exposure with an exposure limit value; and depending on whether the detected exposure is below or above the exposure limit value, activate the magnetic resonance system according to the predetermined measuring sequence or institute other measures.

16. A magnetic resonance system comprising:

a base magnet, a gradient system;

at least one high-frequency coil; and a controller, wherein the controller is configured to activate at least the gradient system and the at least one high-frequency coil, wherein the controller is further configured, during operation, to:

receive parameters of a predetermined measuring sequence from an operator, wherein the parameters define an activation of a gradient system of the magnetic resonance system;

detect an exposure of at least one body region of an examination object brought about by the activation of the gradient system, wherein the detection of the exposure comprises detection of the exposure as a function of a position in which the examination object is disposed in an examination volume of the magnetic resonance system;

store, on a non-transitory computer-readable storage medium, the detected exposure;

compare, by the controller, the detected exposure with an exposure limit value; and depending on whether the detected exposure is below or above the exposure limit value, activate the magnetic resonance system according to the predetermined measuring sequence or institute other measures.

* * * * *